United States Patent
Ferrari

(10) Patent No.: US 6,402,408 B1
(45) Date of Patent: Jun. 11, 2002

(54) COMPOSITION CONTAINING A LIQUID FATTY PHASE GELLED WITH A POLYAMIDE CONTAINING ESTER END GROUPS

(75) Inventor: Véronique Ferrari, Maisons-Alfort (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/618,032

(22) Filed: Jul. 17, 2000

(30) Foreign Application Priority Data

Jul. 15, 1999 (FR) ............................ 99 09176
Jan. 24, 2000 (FR) ............................ 00 00922

(51) Int. Cl.⁷ ............................ A61K 6/00; A61K 7/00; A61K 7/025
(52) U.S. Cl. ..................... 401/64; 424/78.03; 424/64; 424/70.7
(58) Field of Search .................. 424/64, 78.03, 424/401, 70.7

(56) References Cited

U.S. PATENT DOCUMENTS 5,783,657 A * 7/1998 Pavlin et al. ............... 528/310

FOREIGN PATENT DOCUMENTS

GB 2014852 A * 9/1979

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, LLP

(57) ABSTRACT

A composition, in particular a physiologically acceptable composition, comprising at least one liquid fatty phase structured with at least one structuring polymer comprising a polyamide skeleton comprising ester end groups comprising at least one chain chosen from alkyl and alkenyl chains containing from 4 to 42 carbon atoms, combined with at least one amphiphilic compound with a hydrophilic/lipophilic balance (HLB) value of less than 8. This composition can be in the form of a stick of lipstick, even in the absence of wax, can give good impact strength and, when applied, gives a glossy, non-migrating deposit.

75 Claims, No Drawings

COMPOSITION CONTAINING A LIQUID FATTY PHASE GELLED WITH A POLYAMIDE CONTAINING ESTER END GROUPS

The present invention relates to compositions for care of, for treating and for making-up at least one keratinous material, in particular at least one human keratinous material, such as skin, including the scalp, lips, eyelashes and eyebrows, comprising at least one liquid fatty phase gelled with at least one structuring polymer. This invention may be in the form of make-up sticks such as lipsticks and may give a glossy and non-migrating deposit when applied.

Structured liquid fatty phases in cosmetic or dermatological products are known in the art. As used herein, "structured" means gelled and/or rigidified. Structured liquid fatty phases may be found in solid compositions such as deodorants, balms, lip compositions, concealer products and cast foundations. In general, this structuring may be obtained with the aid of waxes or fillers. However, these waxes and fillers have a tendency to make the compositions matte and matte compositions may not be desired. For example, women may desire lip compositions in the form of a tube which deposit glossy films.

As used herein, "liquid fatty phase" means a fatty phase which is liquid at room temperature (25° C.) and at atmospheric pressure (760 mmHg) and which is composed of at least one fatty substance, such as an oil, which is liquid at room temperature. If the liquid fatty phase comprises two or more fatty substances, they should be mutually compatible.

Structured liquid fatty phases may make it possible to control the exudation of the liquid fatty phase from the solid compositions of which they are components. Structuring of the liquid fatty phase may also limit the migration of this phase into wrinkles and fine lines after it has been deposited, for example, on the skin or the lips. A large migration of a liquid fatty phase comprising dyestuffs such as in lip compositions may lead to an unaesthetic effect around the lips which may accentuate the wrinkles and fine lines. Women have cited this migration as a drawback of conventional lip compositions.

The gloss of cosmetic and dermatological compositions may be associated with the nature of the liquid fatty phase. Reduction of the concentration of waxes and fillers in such compositions may increase gloss, but the migration of the liquid fatty phase may increase. In other words, the concentration of waxes and fillers required to prepare cosmetic and dermatological compositions in the form of a stick which have a suitable hardness may limit the gloss of the deposited compositions.

The inventor has found that the observed decrease in gloss of cosmetic and dermatological compositions in the form of a stick which comprise waxes may be associated with the anisotropic crystal structure of the waxes. One aim of the present invention is to provide cosmetic and/or dermatological compositions for the manufacture of wax-free compositions in the form of a stick.

Another subject of the invention is cosmetic and/or dermatological compositions which are useful for the care, make-up and/or treating of at least one keratinous material which may be of suitable hardness to allow preparation of these compositions in the form of a stick, which may be glossy and which may be non-migrating. As used herein, "keratinous material" is meant to comprise hair, lips, skin, scalp and superficial body growths such as eyelashes, eyebrows and nails.

The inventor has found, surprisingly, that the use of specific polymers may make it possible to structure, even, in some embodiments, in the absence of wax, liquid fatty phases in the form of a stick, which may give a glossy and non-migrating film when applied to a keratinous material.

The invention applies not only to make-up products for at least one keratinous material such as lip compositions, lip pencils, foundations which may be cast in the form of a stick or a dish, concealer products, temporary tattoo products, eyeliners which may be in pencil form, mascara tablets, but also to body hygiene products such as deodorant sticks, and to care products and products for treating at least one keratinous material such as sunscreen and after-sun products which may be in stick form. The present invention can be in the form of mascara product, an eyeliner product, a foundation product, a lipstick product, a deodorant product, a make-up product for the body, a make-up-removing product, an eyeshadow product, a face powder product, a concealer product, a treating shampoo product, a hair conditioning product, an antisun product or a care product for the face or the body.

The present invention is also directed to a structured composition comprising at least one liquid fatty phase comprising at least one structuring polymer which comprises a polyamide skeleton comprising at least one end group with at least one chain chosen from alkyl chains comprising at least four carbon atoms and alkenyl chains comprising at least four carbon atoms, bonded to the polyamide skeleton via at least one ester group, the at least one structuring polymer being combined with at least one amphiphilic compound which is liquid at room temperature and has an HLB value of less than 8.

The term "HLB" represents the hydrophilic/lipophilic balance. According to the present invention, one or more amphiphilic compounds that are liquid at room temperature (25° C.) and atmospheric pressure may be used. In one embodiment, the at least one amphiphilic compound has an HLB value ranging from 1 to 7, such as from 1 to 5, further such as from 3 to 5. The purpose of the at least one amphiphilic compound may be to reinforce the structuring properties of the at least one structuring polymer, to facilitate the use of the inventive compositions and to improve the depositability of the inventive compositions, which may be in the form of a stick.

As used herein, "at least one end group" means one or more end groups. As used herein, "polyamide" means at least two repeating amide units.

Due to the at least one chain chosen from alkyl chains and alkenyl chains at the end of the polyamide skeleton, the at least one structuring polymer in the composition of the present invention may have good solubility in oils (i.e. water-immiscible liquid compounds) and thus may give macroscopically homogeneous compositions even with a high content (at least 25%) of the at least one structuring polymer, unlike certain polymers of the prior art that do not contain such alkyl or alkenyl chains at the end of the polyamide skeleton.

The at least one structuring polymer can be chosen from polymers resulting from at least one polycondensation reaction between at least one dicarboxylic acid comprising at least 32 carbon atoms, such as 32 to 44 carbon atoms, with at least one diamine comprising at least 2 carbon atoms, such as from 2 to 36 carbon atoms. The at least one dicarboxylic acid can, for example, be chosen from dimers of at least one fatty acid comprising at least 16 carbon atoms such as oleic acid, linoleic acid and linolenic acid. The at least one diamine can, for example, be chosen from ethylenediamine, hexylenediamine, hexamethylenediamine, phenylenediamine and ethylenetriamine.

The at least one structuring polymer can also be chosen from polymers comprising one or two terminal carboxylic acid groups. The terminal carboxylic acid groups can, for example, be esterified with at least one alcohol chosen from monoalcohols comprising at least 4 carbon atoms. For example, the at least one alcohol can be chosen from monoalcohols comprising from 10 to 36 carbon atoms. In a further example, the monoalcohols can comprise from 12 to 24 carbon atoms, while in yet another example, they can comprise from 16 to 24 carbon atoms.

The composition of the present invention may be in a form chosen from a paste, a solid and a cream. It may be an oil-in-water emulsion, a water-in-oil emulsion, a solid or supple anhydrous gel. The composition can also be in a form chosen from a translucent anhydrous gel and a transparent anhydrous gel. The composition can also be cast as a stick or a dish.

The composition can comprise at least one structuring polymer which has a weight-average molecular mass ranging from 1000 to 10,000 and further such as from 2000 to 8000. This at least one structuring polymer may be a solid which is undeformable at room temperature (25° C.) and atmospheric pressure (760 mmHg). Additionally, this at least one structuring polymer may be capable of structuring the composition without opacifying it.

The at least one structuring polymer can have a softening point greater than 70° C., such as from 70° C. to 190° C., and further such as from 80° C. to 130° C., and even further such as from 80° C. to 105° C. This softening point may be lower than that of structuring polymers known in the art which may facilitate the use of the at least one structuring polymer of the present invention and may limit the degradation of the liquid fatty phase.

The ester groups of the at least one structuring polymer can be present in a proportion ranging from 10% to 50% of the total number of all ester and amide groups in the at least one structuring polymer, such as from 20% to 35%.

The at least one structuring polymer can be chosen from those described in document U.S. Pat. No. 5,783,657 from the company Union Camp, the disclosure of which is incorporated by reference, which are polymers of formula (I):

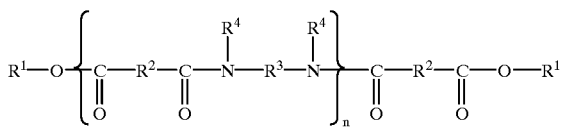

in which:
n is an integer which represents the number of amide units such that the number of ester groups present in said at least one structuring polymer ranges from 10% to 50% of the total number of all said ester groups and all said amide groups comprised in said at least one structuring polymer;

$R^1$, which are identical or different, are each chosen from alkyl groups comprising at least 4 carbon atoms and alkenyl groups comprising at least 4 carbon atoms;

$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In the present invention, n can be an integer ranging from 1 to 5. In the present invention, $R^1$, which are identical or different, can each be chosen from $C_{12}$ to $C_{22}$ alkyl groups, such as from $C_{16}$ to $C_{22}$ alkyl groups.

In the present invention, $R^2$, which are identical or different, can each be chosen from $C_{10}$ to $C_{42}$ alkyl groups. At least 50% of $R^2$, which are identical or different, can each be chosen from groups comprising from 30 to 42 carbon atoms. At least 75% of $R^2$, which are identical or different, can each be chosen from groups comprising from 30 to 42 carbon atoms. In the two aforementioned embodiments, the remaining $R^2$, which are identical or different, can each be chosen from $C_4$ to $C_{19}$ groups, such as $C_4$ to $C_{12}$ groups.

$R^3$, which can be identical or different, can each be chosen from $C_2$ to $C_{36}$ hydrocarbon-based groups and polyoxyalkylene groups. In another example, $R^3$, which can be identical or different, can each be chosen from $C_2$ to $C_{12}$ hydrocarbon-based groups. In another embodiment, $R^4$, which can be identical or different, can each be chosen from hydrogen atoms. As used herein, hydrocarbon-based groups may be linear, cyclic or branched and saturated or unsaturated. As is clear the hydrocarbon-based groups can be aliphatic or aromatic.

According to the present invention, structuring of the at least one liquid fatty phase may be obtained with the aid of at least one structuring polymer of formula (I). The at least one structuring polymer of formula (I) may, of course, be in the form of mixtures of polymers, and these mixtures may also comprise a compound of formula (I) wherein n is equal to zero, i.e. a diester.

Non-limiting examples of at least one structuring polymer which may be used in the composition according to the present include the commercial products sold by the Bush Boake Allen Co. under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

The at least one amphiphilic compound can be chosen from amphiphilic compounds which comprise at least one lipophilic part bonded to at least one polar part. For example, the at least one lipophilic part may comprise a carbon-based chain comprising at least 8 carbon atoms, such as from 16 to 32 carbon atoms and further such as from 18 to 28 carbon atoms.

The at least one polar part, for example, may be chosen from compounds derived from alcohols comprising from 1 to 12 hydroxyl groups, polyols comprising from 2 to 12 hydroxyl groups, and polyoxyalkylenes comprising at least 2 oxyalkylene units. For example, the polyoxyalkylenes comprising at least 2 oxyalkylene units may be chosen from polyoxyalkylenes comprising from 0 to 20 oxypropylene units and from 0 to 20 oxyethylene units.

For example, the at least one amphiphilic compound may be chosen from esters, such as from monoesters and diesters. Representative esters are chosen from hydroxystearates of glycerol, oleates of glycerol, isostearates of glycerol, hydroxystearates of sorbitan, oleates of sorbitan, isostearates of sorbitan, hydroxystearates of methylglucose, oleates of methylglucose, isostearates of methylglucose, hydroxystearates of branched $C_{12}$ to $C_{26}$ fatty alcohols, oleates of branched $C_{12}$ to $C_{26}$ fatty alcohols and isostearates of branched $C_{12}$ to $C_{26}$ fatty alcohols, such as octyldodecanols.

The structuring or gelation of the oils (in general of the at least one liquid fatty phase), which can be modified by the nature of the at least one structuring polymer comprising a polyamide skeleton and that of the at least one amphiphilic compound used, may be such that a rigid structure in the form of a tube or a stick may be obtained.

The concentrations of the at least one amphiphilic compound and of the at least one structuring polymer are chosen according to the desired hardness of the compositions and according to the specific application envisaged. The respective concentrations of the at least one structuring polymer and of the at least one amphiphilic compound can be such that a disintegrable solid which does not flow under its own weight is obtained.

The composition of the present invention may have a hardness ranging from 20 g to 2000 g, such as from 20 g to 900 g, and further such as from 20 g to 600 g. This hardness may be measured according to a method of penetrating a probe into said composition and in particular using a texture analyzer (for example TA-XT2 from Rhéo) equipped with an ebonite cylinder of height 25 mm and diameter 8 mm. The hardness measurement is carried out at 20° C. at the center of 5 samples of said composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 g.

The hardness may also be measured by a "cheese wire" method, which involves cutting an 8.1 mm tube of lip composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may range from 30 g to 150 g, such as from 30 g to 120 g, and further such as from 30 g to 50 g.

The hardness of the composition of the present invention may be such that the compositions are self-supporting and can easily disintegrate to form a satisfactory deposit on a keratinous material. In addition, this hardness may impart good impact strength to the inventive compositions which may be cast in stick form.

According to the present invention, the compositions in stick form may possess the properties of deformable, flexible elastic solids and may have noteworthy elastic softness upon application to a keratinous material. The compositions in stick form of the prior art do not have this elasticity and flexibility.

The at least one structuring polymer (as active material) can be present in a concentration ranging from 0.5% to 80% by weight of the total weight of the composition, such as from 5% to 40%. The at least one amphiphilic compound can be present in a concentration ranging from 0.1% to 35% by weight of the total weight of the composition, such as from 2% to 15%.

When these compositions are colored, they may, after they have been applied to a keratinous material, give a glossy deposit of uniform color which does not migrate into wrinkles or fine lines of the keratinous material.

For example, the at least one liquid fatty phase can comprise greater than 40% by weight of the total weight of said at least one liquid fatty phase of at least one apolar oil, such as greater than 50% by weight. The at least one apolar oil may be chosen from hydrocarbon-based liquid oils.

Representative apolar oils according to the present invention may be chosen from silicone oils such as volatile and nonvolatile, linear, branched and cyclic polydimethylsiloxanes (PDMSs) that are liquid at room temperature; polydimethylsiloxanes comprising groups chosen from alkyl groups, alkoxy groups and phenyl groups, optionally pendant or terminal, and each comprising from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; linear, branched and cyclic, volatile and nonvolatile hydrocarbons and fluorocarbons of synthetic and mineral origin, such as volatile liquid paraffins (such as isoparaffins and isododecane), nonvolatile liquid paraffins and derivatives thereof, petroleum jelly, polydecenes, hydrogenated polyisobutene such as parleam, and squalane. In one embodiment, the apolar oil is chosen from those of the hydrocarbon-based type chosen from mineral and synthetic origin. In another embodiment, the apolar oil is chosen from parleam oil, isoparaffins, squalane and mixtures thereof.

It may be possible to add polar oils to the apolar oils, the apolar oils acting in particular as co-solvent for the polar oils.

Representative polar oils of the present invention may be chosen from:

hydrocarbon-based plant oils having a high content of triglycerides chosen from fatty acid esters of glycerol in which the fatty acids may have varied chain lengths, these chains may be chosen from linear, branched, cyclic, saturated and unsaturated chains. Non-limiting examples of these oils are wheat germ oil, corn oil, sunflower oil, karite butter, castor oil, sweet almond oil, macadamia oil, apricot oil, soybean oil, rape seed oil, cotton oil, alfalfa oil, poppy oil, pumpkin oil, sesame oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil, musk rose oil and caprylic/capric acid triglycerides such as those sold by Stearineries Dubois Co. and those sold under the names Miglyol 810, 812 and 818 by Dynamit Nobel Co.;

synthetic oils and esters of formula $R_5COOR_6$ in which $R_5$ is chosen from linear and branched higher fatty acid groups comprising from 1 to 40 carbon atoms, such as from 7 to 19 carbon atoms; and $R_6$ is chosen from branched hydrocarbon-based groups comprising from 1 to 40 carbon atoms, such as from 3 to 20 carbon atoms, with the proviso that the total number of carbon atoms in $R_5$ and $R_6$ is greater than or equal to 10, such as, for example, in purcellin oil (cetostearyl octanoate), isononyl isononanoate, $C_{12}$–$C_{15}$ alkyl benzoates, isopropyl myristate, 2-ethylhexyl palmitate, alkyl octanoates, polyalkyl octanoates, decanoates ricinoleates, hydroxylated esters such as isostearyl lactate and diisostearyl malate, and pentaerythritol esters; synthetic ethers comprising from 10 to 40 carbon atoms; and $C_8$ to $C_{26}$ fatty alcohols such as oleyl alcohols.

The at least one liquid fatty phase can be present in a concentration ranging from 5% to 99% by weight of the total weight of the composition, such as from 20% to 75% by weight of the total weight of the composition.

The composition of the present invention may further comprise at least one suitable additive commonly used in the field concerned chosen from water optionally thickened or gelled with an aqueous-phase thickener or gelling agent, dyestuffs, antioxidants, essential oils, preserving agents, fragrances, fillers, pasty or waxy fatty substances, neutralizing agents, liposoluble polymers, and cosmetically active agents and dermatological active agents such as, for example, emollients, moisturizers, vitamins, essential fatty acids and sunscreens. The at least one additive is generally present in a concentration ranging from 0% to 20% by weight of the total weight of the composition, such as from 0% to 10%.

Needless to say, the person skilled in the art will take care to select the optional additional additives and the amount thereof such that the advantageous properties of the composition according to the invention, such as gloss and non-migration, are not, or are not substantially, adversely affected by the addition(s) envisaged.

The compositions according to the present invention may be in the form of dermatological or care compositions for at least one keratinous material, such as the skin, the lips and superficial body growths, or in the form of an sunscreen or after-sun composition or a body hygiene composition, such as a deodorant or a make-up removing product. In this case, the compositions may be uncolored, and may optionally comprise cosmetically active agents and/or dermatologically active agents. The composition according to the present invention may be used as a care base for at least one keratinous material such as the skin, superficial body growths or the lips. Non-limiting examples include lip balms for protecting the lips against cold, sunlight or wind and creams for skin, nails or hair.

The composition of the present invention may also be in the form of a colored make-up product for the skin, such as a foundation, optionally having care or treating properties, a blusher, a face powder, an eyeshadow, a concealer product, an eyeliner or a make-up product for the body; a lip make-up such as a lipstick, optionally having care or treating properties; a make-up product for superficial body growths, such as nails or eyelashes, in particular in the form of a tablet of mascara, or for the eyebrows and the hair, such as in the form of a pencil. As is clear, the composition can be in the form of a stick, a pencil, a tablet or a dish.

Needless to say, the composition of the invention should be cosmetically and/or dermatologically acceptable, that is, it should comprise a nontoxic, physiologically acceptable medium which can be applied to at least one human keratinous material. As used herein, "cosmetically acceptable" means having a pleasant appearance, odor and feel.

At least one dyestuff may be chosen from pigments and nacres in order to obtain make-up compositions which give good coverage, that is, which do not leave a significant amount of the at least one keratin material to which it is applied showing through. The pigments may also reduce the sticky feel of the compositions, unlike soluble dyes.

The at least one dyestuff may be representatively chosen from the lipophilic dyes, hydrophilic dyes, pigments and nacres. As used herein, "pigment" means any solid particle which is insoluble in the medium and which serves any of the functions chosen from giving a color, modifying a color, giving an iridescent appearance and modifying an iridescent appearance. The at least one dyestuff is generally present in a concentration ranging from 0.01% to 40% by weight relative to the total weight of said composition, such as from 1% to 35%, and further such as from 5% to 25%.

Representative liposoluble dyes which may be used according to the present invention include Sudan red, DC Red 17, DC Green 6, β-carotene, soybean oil, Sudan brown, DC Yellow 11, DC Violet 2, DC Orange 5 and quinoline yellow. The liposoluble dyes, when present, generally have a concentration ranging up to 20% by weight of the total weight of the composition, such as from 0.1% to 6%.

The pigments which may be used according to the present invention may be chosen from white, colored, mineral, organic, coated and uncoated pigments. Representative examples of mineral pigments include titanium dioxide, optionally surface-treated, zirconium oxide, cerium oxide, iron oxides, chromium oxides, manganese violet, ultramarine blue, chromium hydrate and ferric blue. Representative examples of organic pigments include carbon black, pigments of D & C type, and lakes based on cochineal carmine, barium, strontium, calcium and aluminum. If present, the pigments may have a concentration ranging up to 40% by weight of the total weight of the composition, such as from 1% to 35%, and further such as from 2% to 25%.

The nacreous pigments (or nacres) which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacres, if present, may have a concentration ranging up to 20% by weight of the total weight of the composition, such as from 0.1% to 15%.

The compositions according to the present invention may be manufactured by one of ordinary skill in the art. For example, they may be manufactured by a process which comprises heating the at least one structuring polymer at least to its softening point, adding the at least one amphiphilic compound, the at least one dyestuff, if present, and the at least one suitable additive, if present, to the at least one structuring polymer followed by mixing the composition until a clear, transparent solution is obtained. The resultant homogeneous mixture may then be cast in a suitable mold such as a lipstick mold or cast directly into the packaging articles such as a case or a dish.

The present invention is also directed to a cosmetic process for caring for, making up or treating a keratin material, such as that of a human being, and further such as human skin, comprising the application to a keratin material of a cosmetic composition comprising (a) at least one liquid fatty phase comprising (i) at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group, and (ii) at least one amphiphilic compound which is liquid at room temperature and which has an HLB value of less than 8.

The present invention is also directed to a process of structuring at least one liquid fatty phase in the form of a self-supporting solid having a hardness ranging from 20 g to 2000 g, such as from 20 g to 900 g, and further such as from 20 g to 600 g, comprising including in said at least one liquid fatty phase a sufficient amount of at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group, and of at least one amphiphilic compound which is liquid at room temperature having an HLB value of less than 8, and wherein said self-supporting solid is obtained. For example, this at least one liquid fatty phase may be that of a cosmetic composition.

The present invention is also directed to a process of structuring at least one liquid fatty phase in the form of a glossy and/or nonmigrating solid comprising combining with said at least one liquid fatty phase a sufficient amount of at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group, and at least one amphiphilic compound which is liquid at room temperature and which has an HLB value of less than 8, wherein said glossy and/or nonmigrating solid is obtained.

The present invention is also directed to a process of structuring a cosmetic composition in the form of a physiologically acceptable composition which is glossy and/or nonmigrating comprising including in said composition at least one liquid fatty phase, said at least one liquid fatty phase being structured with at least one structuring polymer which comprises a polyamide skeleton comprising at least one end group with at least one chain chosen from alkyl chains comprising from 4 to 22 carbon atoms and alkenyl chains comprising from 4 to 22 carbon atoms, bonded to said polyamide skeleton via at least one ester group and (ii) at least one amphiphilic compound having an HLB value of less than 8, wherein said glossy and/or nonmigrating cosmetic composition is obtained.

In another embodiment, the present invention is directed to a process of making a cosmetic composition in the form of a physiologically acceptable composition which is glossy and/or nonmigrating comprising including in said composition at least one liquid fatty phase, said at least one liquid fatty phase being structured with at least one structuring polymer which comprises a polyamide skeleton comprising at least one end group with at least one chain chosen from alkyl chains comprising from 4 to 22 carbon atoms and alkenyl chains comprising from 4 to 22 carbon atoms, bonded to said polyamide skeleton via at least one ester group and (ii) at least one amphiphilic compound having an HLB value of less than 8, wherein said glossy and/or nonmigrating cosmetic composition is obtained.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis.

EXAMPLE 1

Lip Composition Formulation

| | |
|---|---|
| Uniclear 80 | 25.0% |
| Parleam oil | 56.0% |
| Polyglyceryl-2 polyhydroxystearate | 10.0% |
| Pigments (brown iron oxide + titanium oxide) | 9.0% |

Preparation: The Uniclear 80 was solubilized (or dissolved) with the aid of the polyglyceryl-2 polyhydroxystearate in the parleam oil, at 100° C., followed by addition of the pigments. The whole was mixed using a deflocculating turbomixer (Rayneri) and then cast in lipstick molds.

A homogeneous stick of lipstick having a hardness of 425 g, measured using a TA-XT2 texture analyzer at 20° C., was obtained. The lipstick obtained was glossy and nonmigrating. This was confirmed by a test with a panel of experts, by comparison with a glossy product of the prior art: Rouge Absolu from Lancôme. The lipstick of the invention was considered by all of the testers as being glossier when applied than the lipstick of the prior art, and as migrating less at time 0 and after being worn for 2 hours.

EXAMPLE 2

Anhydrous Eyeshadow

| | |
|---|---|
| Uniclear 80 | 25.0% |
| Parleam oil | 35.1% |
| Glyceryl oleate | 31.25% |
| Pigments | qs 100% |

This eyeshadow in stick form was prepared as in Example 1. It was glossy and nonmigrating.

Counter Example

The lip composition Example 1 was repeated, replacing the Uniclear 80 polyamide with the Versamid® 930 polyamide sold by the company Henkel, and then by the Macromelt® 6212 polyamide also sold by the company Henkel, these two polyamides being free of an end group with an alkyl or alkenyl chain containing at least 4 carbon atoms, linked to the polyamide skeleton via an ester group.

The products obtained were totally heterogeneous and in two-phase form. They did not in any way have the appearance or hardness of a stick.

What is claimed is:

1. A structured composition comprising: (a) at least one liquid fatty phase comprising:
   (i) at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group; and (ii) at least one amphiphilic compound which is liquid at room temperature and which has an HLB value of less than 8.

2. A composition according to claim 1, wherein said at least one ester group is present in a proportion ranging from 10% to 50% of the total number of all said ester groups and all said amide groups of the at least one structuring polymer.

3. A composition according to claim 1, wherein said at least one structuring polymer has a weight-average molecular mass ranging from 1000 to 10,000.

4. A composition according to claim 3, wherein said at least one structuring polymer has a weight-average molecular mass ranging from 2000 to 8000.

5. A composition according to claim 1, wherein said at least one structuring polymer is chosen from at least one polymer of formula (I):

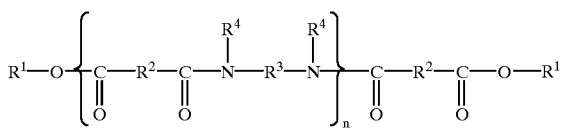

in which:
n is an integer which represents the number of amide units such that the number of ester groups present in said at least one structuring polymer ranges from 10% to 50% of the total number of all said ester groups and all said amide groups comprised in said at least one structuring polymer;

$R^1$, which are identical or different, are each chosen from alkyl groups comprising at least 4 carbon atoms and alkenyl groups comprising at least 4 carbon atoms;

$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

6. A composition according to claim 2, wherein said at least one ester group is present in a proportion ranging from 20% to 35% of the total number of all said ester groups and all said amide groups of the at least one structuring polymer.

7. A composition according to claim 5, wherein said $R^1$, which are identical or different, are each chosen from $C_{12}$ to $C_{22}$ alkyl groups.

8. A composition according to claim 7, wherein said $R^1$, which are identical or different, are each chosen from $C_6$ to $C_{22}$ alkyl groups.

9. A composition according to claim 5, wherein said $R^2$, which are identical or different, are each chosen from $C_{10}$ to $C_{42}$ hydrocarbon-based groups.

10. A composition according to claim 5, wherein said $R^3$, which are identical or different, are each chosen from $C_2$ to $C_{36}$ hydrocarbon-based groups and polyoxyalkylene groups.

11. A composition according to claim 1, wherein said at least one amphiphilic compound comprises at least one lipophilic part bonded to at least one polar part.

12. A composition according to claim 11, wherein said at least one lipophilic part comprises a carbon-based chain comprising at least 8 carbon atoms.

13. A composition according to claim 12, wherein said at least one lipophilic part comprises from 16 to 32 carbon atoms.

14. A composition according to claim 13, where said at least one lipophilic part comprises from 18 to 28 carbon atoms.

15. A composition according to claim 11, wherein said at least one polar part is chosen from compounds derived from alcohols comprising from 1 to 12 hydroxyl groups, polyol groups comprising from 2 to 12 hydroxyl groups, and polyoxyalkylene groups comprising at least 2 oxyalkylene units.

16. A composition according to claim 15, wherein said polyoxyalkylene groups are chosen from polyoxyalkylene groups which comprise from 0 to 20 oxypropylene units and from 0 to 20 oxyethylene units.

17. A composition according to claim 1, wherein said at least one amphiphilic compound is chosen from esters.

18. A composition according to claim 17, wherein said esters are chosen from hydroxystearates of glycerol, oleates of glycerol, isostearates of glycerol, hydroxystearates of sorbitan, oleates of sorbitan, isostearates of sorbitan, hydroxystearates of methylglucose, oleates of methylglucose, isostearates of methylglucose, hydroxystearates of branched $C_{12}$ to $C_{26}$ fatty alcohols, oleates of branched $C_{12}$ to $C_{26}$ fatty alcohols and isostearates of branched $C_{12}$ to $C_{26}$ fatty alcohols.

19. A composition according to claim 18, wherein said branched $C_{12}$ to $C_{26}$ fatty alcohols are chosen from octyldodecanols.

20. A composition according to claim 17, wherein said esters are chosen from monoesters and diesters.

21. A composition according to claim 1, wherein said at least one amphiphilic compound is present in a concentration ranging from 0.1% to 35% by weight of the total weight of said composition.

22. A composition according to claim 21, wherein said at least one amphiphilic compound is present in a concentration ranging from 2% to 15% by weight of the total weight of said composition.

23. A composition according to claim 1, wherein said at least one structuring polymer is present in a concentration ranging from 0.5% to 80% by weight of the total weight of said composition.

24. A composition according to claim 23, wherein said at least one structuring polymer is present in a concentration ranging from 5% to 40% by weight of the total weight of said composition.

25. A composition according to claim 1, wherein said at least one liquid fatty phase comprises greater than 40% by weight of the total weight of said at least one liquid fatty phase of at least one apolar oil.

26. A composition according to claim 25, wherein said at least one liquid fatty phase comprises greater than 50% by weight of the total weight of said at least one liquid fatty phase of at least one apolar oil.

27. A composition according to claim 1, wherein said at least one liquid fatty phase comprises at least one oil.

28. A composition according to claim 27, wherein said at least one oil is chosen hydrocarbon-based oils of mineral origin and hydrocarbon-based oils of synthetic origin.

29. A composition according to claim 1, wherein said at least one liquid fatty phase comprises at least one apolar oil.

30. A composition according to claim 29, wherein said at least one apolar oil is chosen from parleam oil, isoparaffins and squalane.

31. A composition according to claim 1, wherein said at least one liquid fatty phase is present in a concentration ranging from 5% to 99% by weight of the total weight of said composition.

32. A composition according to claim 31, wherein said at least one liquid fatty phase is present in a concentration ranging from 20% to 75% by weight of the total weight of said composition.

33. A composition used to care for at least one keratin material, a composition for treating at least one keratin material, or a make-up composition for at least one keratin material comprising:
   (a) at least one liquid fatty phase comprising:
      (i) at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group; and
      (ii) at least one amphiphilic compound which is liquid at room temperature and which has an HLB value of less than 8.

34. A composition according to claim 1, further comprising at least one dyestuff.

35. A composition according to claim 34, wherein said at least one dyestuff is chosen from lipophilic dyes, hydrophilic dyes, pigments and nacres.

36. A composition according to claim 34, wherein said at least one dyestuff is present in a concentration ranging from 0.01% to 40% by weight relative to the total weight of said composition.

37. A composition according to claim 36, wherein said at least one dyestuff is present in a concentration ranging from 5% to 25% by weight relative to the total weight of said composition.

38. A composition according to claim 1, further comprising at least one suitable additive chosen from water optionally thickened or gelled with an aqueous-phase thickener or gelling agent, antioxidants, essential oils, preserving agents, fragrances, neutralizing agents, liposoluble polymers, cosmetically active agents, dermatologically active agents and waxes.

39. A composition according to claim 1, wherein said composition is in a form chosen from a paste, a solid, a cream, an oil-in-water emulsion, a water-in-oil emulsion and an anhydrous gel, optionally translucent or transparent.

40. A mascara product, an eyeliner product, a foundation product, a lipstick product, a deodorant product, a make-up product for the body, a make-up-removing product, an eyeshadow product, a face powder product, a concealer product, a treating shampoo product, a hair conditioning product, an antisun product or a care product for the face or the body comprising:
   (a) at least one liquid fatty phase comprising:
      (i) at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group; and
      (ii) at least one amphiphilic compound which is liquid at room temperature and which has an HLB value of less than 8.

41. A composition according to claim 1, further comprising at least one pigment.

42. A composition according to claim 1, wherein said at least one amphiphilic compound has an HLB value ranging from 1 to 7.

43. A composition according to claim 42, wherein said at least one amphiphilic compound has an HLB value ranging from 1 to 5.

44. A composition according to claim 43, wherein said at least one amphiphilic compound has an HLB value ranging from 3 to 5.

45. A structured composition comprising a cosmetically acceptable medium and further comprising:
   (a) at least one liquid fatty phase comprising at least one structuring polymer which comprises a polyamide skeleton comprising at least one end group with at least one chain chosen from alkyl chains comprising at least four carbon atoms and alkenyl chains comprising at least four carbon atoms, bonded to said skeleton via an ester group; and
   (b) at least one amphiphilic compound which is liquid at room temperature, with an HLB value of less than 8.

46. A composition according to claim 45, wherein said composition is in cast form.

47. A composition according to claim 45, wherein said composition is in the form of a mascara product, an eyeliner product, a foundation product, a lipstick product, a deodorant product, a make-up product for the body, a make-up-removing product, an eyeshadow product, a face powder product, a concealer product, a treating shampoo product, a hair conditioning product, an antisun product or a care product for the face or the body.

48. A composition according to claim 1, wherein said at least one structuring polymer is chosen from polymers resulting from at least one polycondensation reaction between at least one dicarboxylic acid comprising at least 32 carbon atoms and at least one diamine comprising at least 2 carbon atoms.

49. A composition according to claim 48, wherein said at least one dicarboxylic acid comprises from 32 to 44 carbon atoms.

50. A composition according to claim 48, wherein said at least one diamine comprises from 2 to 36 carbon atoms.

51. A composition according to claim 48, wherein said at least one dicarboxylic acid is chosen from dimers of at least one fatty acid comprising at least 16 carbon atoms.

52. A composition according to claim 48, wherein said at least one fatty acid is chosen from oleic acid, linoleic acid and linolenic acid.

53. A composition according to claim 48, wherein said at least one diamine is chosen from ethylenediamine, hexylenediamine, hexamethylenediamine, phenylenediamine and ethylenetriamine.

54. A composition according to claim 48, wherein said at least one structuring polymer is chosen from polymers comprising one or two terminal carboxylic acid groups.

55. A composition according to claim 54, wherein said terminal carboxylic acid groups are esterified with at least one alcohol chosen from monoalcohols comprising at least 4 carbon atoms.

56. A composition according to claim 55, wherein said at least one alcohol is chosen from monoalcohols comprising from 10 to 36 carbon atoms.

57. A composition according to claim 56, wherein said at least one alcohol is chosen from monoalcohols comprising from 12 to 24 carbon atoms.

58. A composition according to claim 57, wherein said at least one alcohol is chosen from monoalcohols comprising from 16 to 24 carbon atoms.

59. A composition according to claim 1, wherein said at least one structuring polymer has a softening point of greater than 70° C.

60. A composition according to claim 59, wherein said at least one structuring polymer has a softening point of 70° C. to 1 90° C.

61. A composition according to claim 60, wherein said at least one structuring polymer has a softening point of 80° C. to 130° C.

62. A composition according to claim 61, wherein said at least one structuring polymer has a softening point of 80° C. to 105° C.

63. A composition according to claim 5, wherein said n is an integer ranging from 1 to 5.

64. A composition according to claim 5, wherein said n is equal to zero.

65. A composition according to claim 1, wherein said composition has a hardness ranging from 20 g to 2000 g.

66. A composition according to claim 65, wherein said composition has a hardness ranging from 20 g to 900 g.

67. A composition according to claim 66, wherein said composition has a hardness ranging from 20 g to 600 g.

68. A cosmetic process for caring for, making up or treating a keratin material comprising the application to at least one keratinous material of a cosmetic composition comprising:
 (a) at least one liquid fatty phase comprising:
  (i) at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group; and
  (ii) at least one amphiphilic compound which is liquid at room temperature and which has an HLB value of less than 8.

69. A process of structuring a liquid fatty phase in the form of a self-supporting solid comprising including in said at least one liquid fatty phase a sufficient amount of (i) at least one structuring polymer comprising a polyamide skeleton which comprises at least one end group with at least one chain chosen from alkyl chains comprising at least 4 carbon atoms and alkenyl chains comprising at least 4 carbon atoms, bonded to said polyamide skeleton via at least one ester group, and (ii) at least one amphiphilic compound which is liquid at room temperature having an HLB value of less than 8; and wherein said self-supporting solid is obtained.

70. A process according to claim 69, wherein said self-supporting solid has a hardness ranging from 20 g to 2000 g.

71. A process according to claim 70, wherein said self-supporting solid has a hardness ranging from 20 g to 900 g.

72. A process according to claim 71, wherein said self-supporting solid has a hardness ranging from 20 g to 600 g.

73. A process of structuring at least one liquid fatty phase in the form of a glossy and/or nonmigrating solid comprising combining with said at least one liquid fatty phase a sufficient amount of (i) at least one structuring polymer comprising a polyamide skeleton which comprises at least one end group with at least one chain chosen from alkyl chains comprising at least four carbon atoms and alkenyl chains comprising at least four carbon atoms, bonded to said polyamide skeleton via at least one ester group, and (ii) at least one amphiphilic compound which is liquid at room temperature having an HLB value of less than 8;
 wherein said glossy and/or nonmigrating solid is obtained.

74. A process of structuring a cosmetic composition in the form of a physiologically acceptable composition which is glossy and/or nonmigrating comprising including in said composition at least one liquid fatty phase, said at least one liquid fatty phase being structured with at least one structuring polymer which comprises a polyamide skeleton comprising at least one end group with at least one chain chosen from alkyl chains comprising from 4 to 22 carbon atoms and alkenyl chains comprising from 4 to 22 carbon atoms, bonded to said polyamide skeleton via at least one ester group and (ii) at least one amphiphilic compound having an HLB value of less than 8;
 wherein said glossy and/or nonmigrating cosmetic composition is obtained.

75. A process of making a cosmetic composition in the form of a physiologically acceptable composition which is glossy and/or nonmigrating comprising including in said composition at least one liquid fatty phase, said at least one liquid fatty phase being structured with at least one structuring polymer which comprises a polyamide skeleton comprising at least one end group with at least one chain chosen from alkyl chains comprising from 4 to 22 carbon atoms and alkenyl chains comprising from 4 to 22 carbon atoms, bonded to said polyamide skeleton via at least one ester group and (ii) at least one amphiphilic compound having an HLB value of less than 8;
 wherein said glossy and/or nonmigrating cosmetic composition is obtained.

* * * * *

UNITED STATES PATENT AND TRADEMARK OFFICE
CERTIFICATE OF CORRECTION

PATENT NO.     : 6,402,408 B1                                             Page 1 of 1
DATED          : June 11, 2002
INVENTOR(S)    : Véronique Ferrari It is certified that error appears in the above-identified patent and that said Letters Patent is hereby corrected as shown below:

Column 11,
Line 66, "$C_6$" should read -- $C_{16}$ --.

Column 15,
Line 15, "1 90" should read -- 190 --.

Signed and Sealed this

Eighth Day of October, 2002

*Attest:*

JAMES E. ROGAN
*Attesting Officer*    *Director of the United States Patent and Trademark Office*